(12) United States Patent
Ustuner et al.

(10) Patent No.: US 10,064,602 B2
(45) Date of Patent: Sep. 4, 2018

(54) COHERENCE ULTRASOUND IMAGING WITH BROAD TRANSMIT BEAMS

(71) Applicant: Siemens Medical Solutions USA, Inc., Malvern, PA (US)

(72) Inventors: Kutay F. Ustuner, Mountain View, CA (US); Nicholas Bottenus, Durham, NC (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 607 days.

(21) Appl. No.: 14/596,069

(22) Filed: Jan. 13, 2015

(65) Prior Publication Data

US 2015/0342567 A1 Dec. 3, 2015

Related U.S. Application Data

(60) Provisional application No. 62/007,204, filed on Jun. 3, 2014.

(51) Int. Cl.
| | |
|---|---|
| *A61B 8/08* | (2006.01) |
| *A61B 8/14* | (2006.01) |
| *A61B 8/00* | (2006.01) |
| *G10K 11/34* | (2006.01) |
| *G01S 15/89* | (2006.01) |
| *G01S 7/52* | (2006.01) |

(52) U.S. Cl.
CPC .............. *A61B 8/5207* (2013.01); *A61B 8/14* (2013.01); *A61B 8/4483* (2013.01); *A61B 8/4488* (2013.01); *A61B 8/48* (2013.01); *G01S 15/8915* (2013.01); *G01S 15/8977* (2013.01); *G10K 11/346* (2013.01); *G01S 7/52049* (2013.01)

(58) Field of Classification Search
CPC ............... G10K 11/346; G01S 15/8915; G01S 7/52049; G01S 15/8977; A61B 8/4483; A61B 8/48; A61B 8/5207; A61B 8/4488; A61B 8/14

See application file for complete search history.

(56) References Cited

U.S. PATENT DOCUMENTS

| | | | | |
|---|---|---|---|---|
| 4,127,034 | A * | 11/1978 | Lederman | .............. G01N 29/06 367/7 |
| 7,744,532 | B2 | 6/2010 | Ustuner et al. | |
| 2005/0033165 | A1* | 2/2005 | Ustuner | ............... A61B 8/5269 600/437 |
| 2005/0228279 | A1* | 10/2005 | Ustuner | .............. G01S 15/8927 600/443 |

(Continued)

OTHER PUBLICATIONS

R. Mallart et al., "The van Cittert-Zernike theorem in pulse echo measurements," The Journal of the Acoustical Society of America, vol. 90, no. Nov. 1991.

(Continued)

*Primary Examiner* — Bo J Peng

(57) ABSTRACT

Acoustic reciprocity between transmit and receive is used for coherence ultrasound imaging. Rather than finding coherence across the receive channels, coherence is found across transmit channels. Broad transmit beams are used for different transmit elements or apertures to create beamformed frames of data. The coherence between these transmit channel frames of beamformed data is calculated and used for imaging.

19 Claims, 4 Drawing Sheets

(56) References Cited

U.S. PATENT DOCUMENTS

| | | | |
|---|---|---|---|
| 2006/0173313 A1* | 8/2006 | Liu | G01S 7/52046 600/437 |
| 2006/0241429 A1 | 10/2006 | Ustuner et al. | |
| 2008/0183079 A1* | 7/2008 | Lundberg | G01S 7/52085 600/443 |
| 2009/0069693 A1* | 3/2009 | Burcher | G01S 7/52028 600/459 |
| 2013/0109971 A1* | 5/2013 | Dahl | A61B 8/08 600/447 |
| 2014/0046187 A1* | 2/2014 | Taniguchi | A61B 8/5269 600/444 |

OTHER PUBLICATIONS

D.-L. Liu et al., "About the Application of the Van Cittert-Zernike Theorem in Ultrasonic Imaging," IEEE Transactions on Ultrasonics, Ferroelectrics, and Frequency Control, vol. 42, No. 4, pp. 590-601, Jul. 1995.

R. Mallart et al., "Adaptive focusing in scattering media through sound-speed inhomogeneities: The van Cittert Zernike approach and focusing criterion," The Journal of the Acoustical Society of America, vol. 96, No. 6, pp. 3721-3732, 1994.

D.-L. Liu et al., "Estimation and correction of ultrasonic wavefront distortion using pulse-echo data received in a two-dimensional aperture." IEEE transactions on Ultrasonics, Ferroelectrics, and Frequency Control, vol. 45, No. 2, pp. 473-490, Jan. 1998.

P.-C. Li et al., "Adaptive Imaging Using the Generalized Coherence Factor," IEEE Transactions on Ultrasonics, Ferroelectrics and Frequency Control, vol. 50, No. 2, pp. 128-141, 2003.

J. Camacho et al., "Phase Coherence Imaging," IEEE Transactions on Ultrasonics, Ferroelectrics, and Frequency Control, vol. 56, No. 5, pp. 958-974, May 2009.

M. A. Lediju et al., "Shortlag spatial coherence of backscattered echoes: imaging characteristics." IEEE Transactions on Ultrasonics, Ferroelectrics, and Frequency Control, vol. 58, No. 7, pp. 1377-1388, Jul. 2011.

D. Hyun et al., "In vivo demonstration of a realtime simultaneous B-mode/spatial coherence GPU-based beamformer," 2013 IEEE International Ultrasonics Symposium (IUS), pp. 1280-1283, Jul. 2013.

J. A. Jensen et al., "Sarus: A synthetic aperture real-time ultrasound system," IEEE Transactions on Ultrasonics, Ferroelectrics, and Frequency Control, vol. 60, 2013.

* cited by examiner

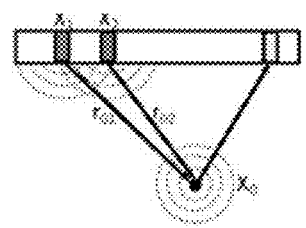
FIG. 2
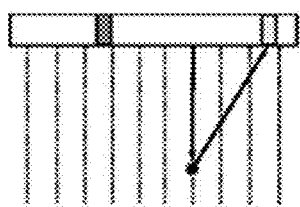 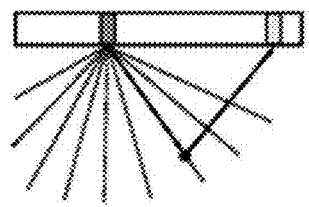 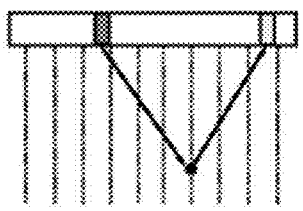
FIG. 3A  FIG. 3B  FIG. 3C
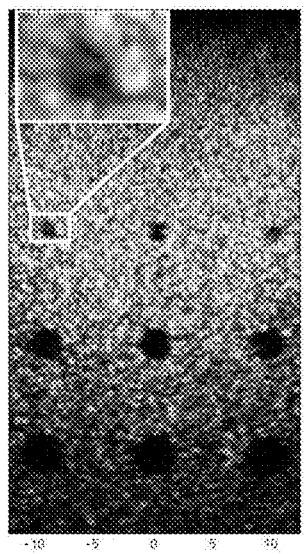 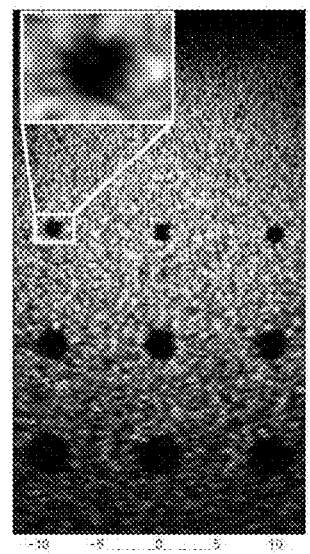 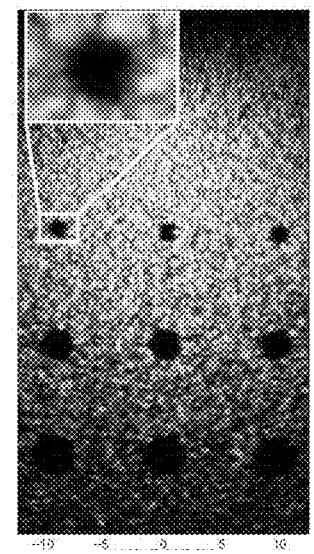
FIG. 4A  FIG. 4B  FIG. 4C

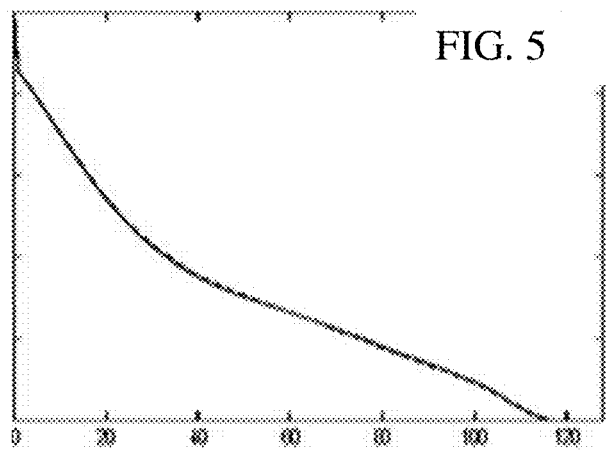
FIG. 5
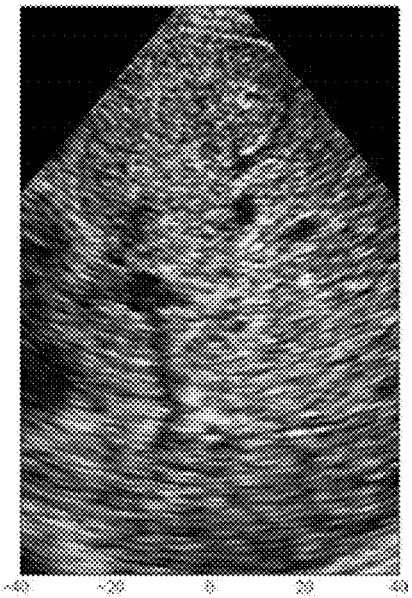
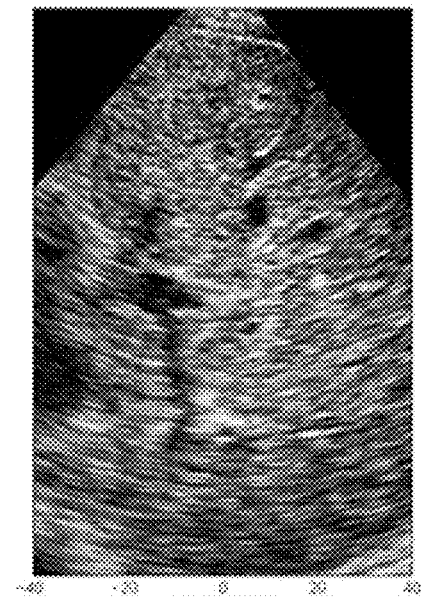
FIG. 6A　　　　　　　　FIG. 6B

COHERENCE ULTRASOUND IMAGING WITH BROAD TRANSMIT BEAMS

RELATED APPLICATIONS

The present patent document claims the benefit of the filing date under 35 U.S.C. § 119(e) of Provisional U.S. Patent Application Ser. No. 62/007,204, filed Jun. 3, 2014, which is hereby incorporated by reference.

BACKGROUND

This present invention relates to coherence ultrasound imaging. Ultrasound images are formed by transmitting sound waves from an array and receiving echoes backscattered from the body using the same array. A beamformer applies receive focal delays to the individual channel signals from elements of the array and coherently sums the signals across element channels to form samples representing a scan line. The summed data is then detected and scan converted to form an image, such as B-mode image. For further processing, only the summed signals may be available in many ultrasound systems.

Element channel data may enable alternative beamforming methods that examine the incoming signal across the receiving array. The Van Cittert-Zernike (VCZ) theorem describes the expected coherence of the return signals scattered from diffuse media. For a uniform, diffuse medium, the coherence of echoes backscattered from the focal point as a function of receive element separation, or lag, is given by the Fourier transform of the square of the transmit pressure field magnitude. Therefore, the expected coherence of an aperture with unity weighting across the array is a ramp function that predicts decreasing covariance for increasing lag value. Short-lag spatial coherence (SLSC) imaging takes advantage of the coherence measurement by estimating the coherence curve as a function of lag and integrating the curve up to a small fraction of the aperture length to form an image.

Previous implementations of a real-time SLSC imaging system utilize a research scanner with access to receive channel data. However, translation of coherence methods to more widely-available clinical scanners with more developed post-processing pipelines may not occur. Most clinical scanners do not provide access to receive channel data.

BRIEF SUMMARY

By way of introduction, the preferred embodiments described below include methods, computer readable storage mediums, and systems for coherence ultrasound imaging. Acoustic reciprocity between transmit and receive is used. Rather than finding coherence across the receive channels, coherence is found across transmit channels. Broad transmit beams are used for different transmit elements or apertures to create beamformed frames of data. The coherence between these transmit channel frames of beamformed data is calculated and used for imaging.

In a first aspect, a method is provided for coherence ultrasound imaging. A transducer transmits first and second broad transmit beams at different angles. The first and second broad transmit beams cover an overlapping region. First and second sets of signals responsive to the first and second transmit beams, respectively, are received with the transducer. A beamformer beamforms first and second frames of data representing the overlapping region from the first and second sets of signals, respectively. A processor calculates covariance or correlation between the data of the first and second frames for each of a plurality of locations in the overlapping region. An image of a measure of the covariance or correlation for each of the locations is generated.

In a second aspect, a system is provided for coherence ultrasound imaging. A transmit waveform generator is configured to sequentially insonify, using an array of elements, a region with broad beams from different transmit apertures. A receive beamformer is configured to generate beamformed sets of coherent data responsive to the insonifications from the different transmit apertures. A processor is configured to measure coherence at different locations of the region between the beamformed sets of coherent.

In a third aspect, method is provided for coherence ultrasound imaging. Tissue is insonified with first and second broad beams at first and second angles, respectively, from first and second transmit elements. First and second data sets are received in response to the first and second broad beams, respectively. First and second transmit element images are formed by focusing. The first and second transmit element images represent a plurality of spatial locations. Covariance of the first and second transmit element images is measured. An image representing a characteristic of the covariance at the spatial locations is displayed.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 2 shows an example of two transmit elements for insonifying a location;

FIGS. 3A-C shows different example receive beamformation patterns;

FIGS. 4A-C show different imaging effects associated with the different receive beamformation patterns of FIGS. 3A-C, respectively;

FIG. 5 shows an example covariance as a function of lag;

FIGS. 6A and 6B show example liver images generated with covariance measures;

DETAILED DESCRIPTION OF THE DRAWINGS AND PRESENTLY PREFERRED EMBODIMENTS

Figure 1:
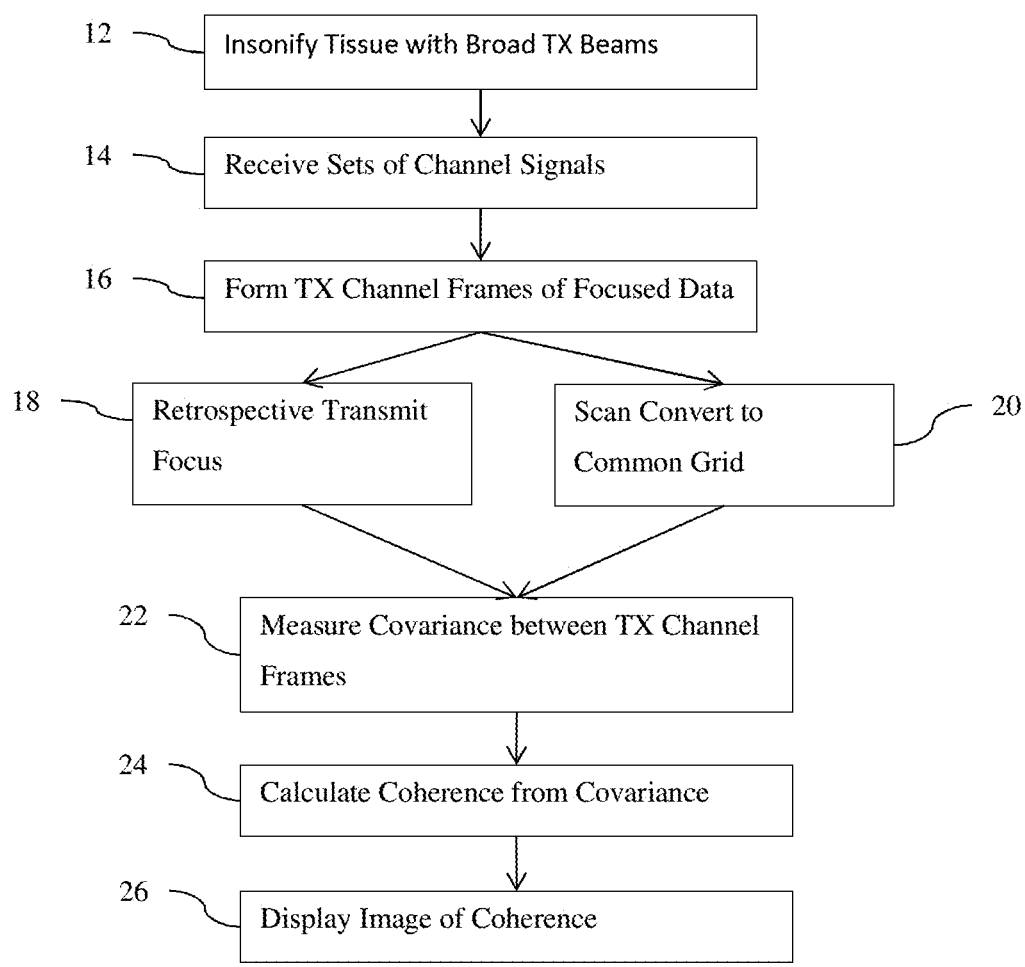
FIG. 1 is a flow chart diagram of one embodiment of a method for coherence ultrasound imaging.

Acoustic reciprocity is used in spatial coherence ultrasound imaging. To accommodate conventional ultrasound systems, beamforming is implemented. Using coherence across transmit images of beamformed data may provide similar imaging as receive channel coherence. Coherence imaging applications, such as a generalized coherence factor, phase coherence imaging, or SLSC imaging, may be provided.

In a generalized form, the cross correlation of transmit channel frames of beamformed data (e.g., frame of image data or other data set), s[m,x,z], for every transmit channel m is computed, creating a N-curve correlation set. The N-curve correlation set, ρ, is represented as:

$$\rho(m,n,x,z) = \Sigma_{r(x,z)}(s(m,x,z)s^*(m+n,x,z))$$

where s* is the complex conjugate of s, z is depth or axial dimension, and x is lateral location.

The correlation curve set is averaged over all m that have the same lag n to create:

$$\rho[n,x,z] = <\rho[m,n,x,z]>,$$

where <.> is the average over m. ρ[n,x,z] approximates a triangle with a width 2N−1 if the effective receive apodization is uniform and if the object within the correlation region is incoherent, such as soft tissue. A B-Mode image of soft tissue has fully developed speckle. ρ[n,x,z] becomes flat for a strong small isotropic target. ρ[m,n,x,z] is a spikey function with a narrow span in n if the object is specular. Specular targets such as surfaces, membranes, tendons, or others are in a spatially narrow band and hence are anisotropic. For this class of objects, the correlation set ρ[m,n,x,z] shows a strong peak at channel $m_0$ and gets weaker rapidly away from channel $m_0$ where $m_0$ is the channel closer to the normal of the specular target at [x,z].

Using this coherence across transmit images (e.g., frames of beamformed data from different transmits), various types of imaging may be provided. Short lag, spatial correlation imaging is one type. After discussion of some of the types of imaging below, the disclosure provides further details about the short lag, spatial correlation (SLSC) approach. SLSC is represented as:

$$SLSC[x,z] = \Sigma_{n=0}^{M} \hat{\rho}[n,x,z],$$

where M<N and $\hat{\rho}$ is ρ derived from a normalized set of a channel correlation set, represented as:

$$\hat{\rho}[m, n, x, z] = \frac{\rho[m, n, x, z]}{\sqrt{\Sigma_r |s[m, x, z]|^2 \Sigma_r |s[m + n, x, z]|^2}}.$$

Another type of imaging is of incoherent isotropic objects, such as images of speckle. The image, I, is given by:

$$I[x, z] = \Sigma_n \frac{\rho(n, x, z)}{\rho(0, x, z)(N - n)}.$$

To prevent noise amplification by the 1/(N−n) term, the summation may be terminated at n<N, e.g., n=2N/3.

Yet another type of imaging is of specular anisotropic objects. This image, I, is computed as:

$$I[x,z] = \max_m \Sigma_n \Sigma[m,n,x,z],$$

Another type of imaging is the direction of anisotropic objects. This image, I, is computed as:

$$I[x,z] = m_0(x,z),$$

where $m_0$ is the m where $\Sigma_n$ ρ[m, n, x, z] peaks. $m_0$ may be color or gray scale coded.

The image may alternatively be a combination of any of the types of imaging. Overlays, averaging, value selection per location, or other combinations may be used. Once the image is calculated as a frame of data, other processing may be applied to derive image values for the display, such as scan conversion, color mapping, gray scale mapping, or filtering.

For SLSC, a conventional ultrasound image is formed by transmitting a focused wave into tissue, time-shifting the backscattered echoes received on an array transducer and summing the resulting signals. The Van Cittert-Zernike theorem predicts a particular similarity, or coherence, of these focused signals across the receiving array. The estimate of the coherence may be used to augment or replace the B-mode image in an effort to suppress noise and stationary clutter echo signals, but this measurement relies on access to individual receive channel data. Most clinical ultrasound systems have efficient pipelines for producing focused and summed data without any direct way to individually address the receive channels. Using transmit and receive reciprocity, the coherence is found between frames of beamformed data associated with different broad transmit beams to the same region. Coherence measurements based on beamformed data that is more accessible is provided for a wide range of coherence-based imaging.

FIG. 1 shows a method for coherence ultrasound imaging. The method is implemented by the system 10 of FIG. 8 or a different system. Acts 12, 14, and 16 are performed with an ultrasound scanner, such as an imaging system including a transducer and receive beamformer. Acts 18, 22, and 24 are performed by a processor, such as a processor of an ultrasound scanner or a separate computer. Act 20 is performed by the processor or a scan converter. Act 26 is performed by a processor in combination with a display. Other devices may perform any one or more of the acts.

Additional, different or fewer acts may be provided. For example, acts 18 and/20 are not provided. As another example, acts 22 and 24 are combined into one act where the measured covariance is used as the coherence. In yet another example, act 26 is not provided and/or other acts for aberration correction are provided. The coherence may be used to identify aberrations in the field of view and correct the delays or phases applied in beamforming to account for the aberrations. The acts are performed in the order shown or a different order.

In act 12, an ultrasound scanner insonifies tissue with broad beams. Broad beam transmissions include unfocused (e.g., diverging) or weakly focused ultrasonic waves that insonify a region, such as a majority of a two dimensional region to be scanned, from one or more angles. A virtual point source (e.g., virtual element) may be used at a large, substantially infinite or other distance behind an array to define a broad transmit beam. The virtual point source may be moved laterally relative to the array to steer the broad transmit beam. A virtual source element located behind the array may increase the channel signal-to-noise ratio as compared to using a transmit element sourced on the array (actual element).

To compensate for undesired divergence, a mildly focused planar wave may be generated as the broad transmit wavefront. The energy generated by each element of the transducer array is delayed relative to other elements to steer or mildly focus a plane wave. A Gaussian or hamming apodization function is applied across the transducer array to reduce edge waves generated by the finite aperture provided by the transducer array. Other techniques for generating plane waves, such as using other types of apodization or using a mildly diverging plane wave may be used. In other embodiments, one, two, or a small number (e.g., less than five)

elements are used for each transmit, providing a diverging beam or acoustic energy field as the broad beam.

Using transmit elements of a transducer array, acoustic energy is transmitted. Any number of such broad beam transmissions may be used, such as two or more. For example, tens or hundreds of broad beam transmissions are performed. Each transmission is from a different transmit aperture, such as a different transmit element or different combination of transmit elements. The elements are real or virtual elements. Due to the transmit apertures being different for the sequential broad beams, the angle at which the scan region is insonified is different. The transmissions are from different angles to scan the same locations.

Each of the broad transmit beams covers a majority of a two-dimensional plane across a scanned region. Alternatively, a lesser area is covered. A single broad transmit beam may allow formation of an image of the entire region of interest, resulting in a high frame rate. Alternatively, multiple transmissions to different areas scan an entire region of interest. The scan is for two or three-dimensional imaging. The broad transmit beam may extend along two or three-dimensions. The scan is repeated for the same locations so that acoustic response for the same locations from different transmit apertures is provided. Different scans scan an overlapping region of the field of view.

FIG. 2 shows a simplified example. FIG. 2 is simplified in showing only two transmit apertures, single transmit element $X_1$ and $X_2$, where there may be many more and/or more complex transmit apertures for generating the broad beam. For example, sixty four or more (e.g., 112) broad beams are transmitted to cover the same locations or overlapping region from different transmit apertures spaced along the transducer array. In the example of FIG. 2, the response from one location to both broad transmits as received at a single element is represented, but the response from other locations to a larger (e.g., entire array or majority of elements) receive aperture may be used. For transmit channel coherence, a signal is transmitted from two different transmit sources, scattered and received using a focused group of receive elements.

Any spacing of the transmit apertures may be used, such as using each element along an array as a separate transmit aperture. Every other or other spacing may be used. The amount of sparsity chosen presents a trade-off between faster acquisition and more thorough sampling of the coherence function.

The transmitted broad beam has any frequency, such as a center frequency of 1-10 MHz (e.g., 3.2 MHz). Any amplitude and/or apodization may be used. Square waves or sinusoidal waves may be used. Any number of cycles, such as 1-3 cycles, may be used.

In act 14, channel signals are received. In response to the transmitted acoustic energy, echoes return to the transducer. The elements of the transducer convert the acoustic energy into electrical signals. As echoes return from deeper depths, each element of the receive aperture generates a waveform over time. The collection of such waveforms over time in response to a given insonification or broad beam by the different elements provides a set of signals. The set of signals are receive channel data where each element forms a reception channel. By receiving a set of signals for each transmit beam, different sets of signals or data sets responsive to the broad transmit beams are provided. For example, the receive aperture is 64 or more elements. A set of signals for one broad beam transmit is channel data for the 64 or more elements. Another set for another broad transmit beam is channel data for the 64 or more elements.

The same receive aperture is used for receiving the channel data from the different broad transmit beams. The elements used for receive operation are the same for each of the broad transmit beams covering the same locations. In alternative embodiments, the receive aperture varies with transmit beam, such as altering the number, spacing, and/or position of the receive aperture based on the different angles of the transmit beams.

Different receive apertures may be used for different regions. For example, four broad beams from a given angle or transmit aperture are used to scan four adjacent regions (e.g., the region of interest is divided into and scanned in four parts). For receive operation, channel data is received in response to each of broad transmit beams. Due to the different locations being scanned, different receive apertures may be used for the different regions.

The scan geometry may include more receive beams or perform faster scans with reduced sampling or a narrower field of view. Fewer or more transmit beams and corresponding receive channel data may be provided with a tradeoff between sampling of the coherence and speed of imaging.

In act 16, transmit element frames of data are formed by focusing. Each transmit element frame represents a plurality of spatial locations, such as being a frame of data representing sample locations. The received channel data of a set is used to form a frame of data representing a two or three-dimensional region of the patient.

Any focusing may be used. In one embodiment, a Fourier transform based approach is used. In another embodiment, a receive beamformer applies receive beamforming. The channel data is dynamically focused as received or based on stored signals. Channel signals from the elements are relatively apodized and delayed or phase shifted. The results are summed. The delay or phase shift varies over time or depth, providing dynamic receive focusing.

A transmit element frame is created for each transmit beam or group of beams used to scan the region of interest or field of view once. The transmit element frames of data are formed to represent spatial locations of the scanned region. The data includes values representing a plurality of locations in a scanned region. Frames of data include data associated with a particular scan or combinations of scans. A frame of data includes data representing the region of interest whether or not the data is in a frame format. Different transmit element frames represent the same overlapping region at different times. Coded excitations may be used to acquire different transmit element frames representing the overlapping region at a same time.

Each set or frame of data may be denoted mathematically as $S_n(x,y)$, where (x,y) is a point in the image and n represents a specific transmit and receive function settings. For example, the transmit aperture function varies as a function of virtual point sources at different positions. A first set of data is obtained with a broad transmit beam transmitted at a first angle relative to the array, and a second set of data is obtained with a broad transmit beam transmitted at a second, different angle relative to the array.

The obtained focused data includes phase information. The data are in a radio frequency (RF) or in-phase and quadrature (IQ) format. The image or beamforming process results in samples from different locations. Each of the samples includes phase and magnitude information.

Any number of receive scan lines may be used for a given broad transmit beam. In the beamforming example, two, four, eight, sixteen or more receive beams are formed for each broad transmit beam. The transmit beam is broad enough to cover multiple receive scan lines. For example, 64 equally spaced receive beams are formed over an 80 degree field of view using sixteen parallel receive beams for a respective four broad transmit beams, such as four identical broad transmit beams. This combination provides one frame of data. Other frames of data for the field of view are formed using different transmit apertures. The parallel receive beamforming may not impact image quality and may be used to the maximum extent to which a receive beamformer is capable.

Each transmit element frame represents the field of view from a different transmit aperture. The transmit element frames may be treated as transmit channel data sets. A transmit channel data set may be directly acquired by performing a conventional synthetic aperture scan, transmitting on a single element and recording data for all desired receive beams either over multiple transmit events or using parallel receive beamforming. The system performs receive focusing and sums the receive channel data, producing the transmit channel data set s[z,x,tx], where tx is the transmit aperture index. The coherence may be calculated from the transmit channel data.

Different scan formats to acquire a frame may be used. FIGS. 3A-C show examples of three acquisition sequences and beamforming approaches compatible with a clinical scanner architecture. Each FIG. 3A-C shows the active transmit element (dark) and a sample receive element (grey). Other sequences may be used.

FIG. 3A shows beamforming along a rectilinear field of view with transmit correction. The same rectilinear field of view is used for each of the transmit apertures such that the resulting data completely overlaps. This uses unique receive delays corresponding to every transmit element. It is assumed that the scanner calculates delays along the specified receive beamforming line and back to each receive element individually. The field of view and beam forming geometry is shown in FIG. 3A. Even though receive beamforming is performed on the scanner, this data set still uses further transmit focusing to compensate for the difference in path length between the true transmit distance (e.g., the line from the transmit element to the point of interest) and the receive beamline. Once the receive channels have been summed, each beamformed sample describes a particular receive focus. Using synthetic transmit focusing, the summed data of the frame is resampled to provide a transmit delay adjustment. Act 18 of FIG. 1 provides this retrospective transmit focusing of the data of the transmit element frames.

Resampling the summed data to perform the transmit delay adjustment may introduce errors in the receive delay curvature by selecting a sample that describes a different receive focus. This creates focal errors that are more severe closer to the transducer, where the receive delay curvature changes more quickly through depth. FIG. 4A shows a resulting short lag spatial coherence (SLSC) image and demonstrates artifacts that obscure the speckle texture close to the transducer and the shallowest set of lesions.

FIGS. 4A-C are generated with experimental transmit element channel data. The inset in each figure shows a shallow anechoic lesion. The lesion displayed in the inset shows clutter. In FIG. 4A, there is an angular streaking especially in the outer pair of lesions caused by the incorrect receive focus curvature. The artifact is less noticeable after the first few centimeters, and no artifact is apparent in the middle set of lesions. A compromise may be made between transmit and receive focal quality. Further corrections may be performed or the artifact is deemed acceptable.

FIG. 3B shows another approach with beamforming over a fan format. A shifting fan-beam field of view is used. The region where the fan-beams overlap is the effective field of view. A more complete synthetic aperture calculation may be made by positioning the receive beamforming lines such that the receive lines are collinear with lines drawn from the active transmit element or aperture to the points of interest in the field. The receive beams are positioned in a fan-beam around the active transmit element, as if performing phased array focusing. Phased array scanning is supported by many scanners, but the field of view is translated to be centered on the active transmit element.

While no additional focusing is required, scan conversion is used to deal with the shifting fan format. In act 20 of FIG. 1, the transmit element frames of data are scan converted to a common grid of locations. A scan converter converts the beamformed data from the different transmit apertures onto the same rectilinear or other grid for post-processing. Bilinear or other interpolation is used. Parallel processing for each frame may speed conversion from the scan format to a common format (e.g., Cartesian coordinate). In order to maintain coherence in the scan conversion from a polar coordinate system to a Cartesian grid, the signal is sampled both in range and angle to satisfy the Nyquist criteria. FIG. 4B demonstrates a SLSC image generated using this format. The scan conversion has only a small effect on the image quality. There is a slight blurring of the texture at depth, but there are no artifacts within the anechoic targets.

FIG. 3C shows a rectilinear field of view with ideal focusing. Independent receive delays are specified for each transmit and receive element both axially and laterally. Full synthetic aperture delays are calculated by the system, and the data is recorded on the same rectilinear grid, removing the need for scan conversion. This method may not be compatible with the standard receive beam forming line definition since the transmit and receive paths are not collinear. FIG. 4C shows a SLSC image generated using this format.

Frames of data representing acoustic response to different respective broad transmit beams are provided. For coherence imaging, the coherence between these different transmit channels or transmit element frames is found. The coherence across the frames of coherent data is calculated. In act 22, a processor calculates covariance between the data of the frames. The covariance is measured across or between the different transmit channels or transmit element frames.

Any covariance calculation may be used to measure. In one embodiment, a correlation, such as a cross-correlation is used. For example, a normalized cross-correlation or a correlation with a mean subtracted is calculated. Normalized cross-correlation is performed across the transmit channels to measure a coherence curve. Correlation coefficients are a measure of covariance.

The coherence curve as a function of lag is determined. FIG. 5 shows an example of normalized correlation as a function of lag. In the example of FIG. 5, 112 different transmit elements or apertures are used, resulting in lag calculations based on the 112 transmit element frames. Other numbers may be provided. The curve shows the normalized cross-correlation as a function of lag.

The covariance is calculated for each location in the field of view, region of interest, or overlap region. A curve or lag calculation is provided for each location. The data across the frames for a given location is used. In other embodiments, a spatial kernel centered at the location is used. The covariance across or between frames for the data designated by the kernel in each frame is used. The covariance at other locations is found by placing the kernel appropriately. The covariance is calculated for each of a plurality of locations in the overlapping region or throughout the field of view. Curves or values are calculated using the different frames associated with the different broad transmit beams. The beamformed or other image formed data is used in the calculation, so the covariance calculation is performed on RF or IQ with phase information.

In act 24, the coherence is calculated from the covariance information. For each spatial location, a value of coherence is determined from the covariance for the respective location. Any function may be used. For example, a value representing the amount of covariance is used. As another example, a characteristic of the correlation as a function of lag is used. For example, a short lag spatial coherence is calculated. An integral, sum, or average of lags over less than the entire available lag is calculated. The short lag may be five or less, ten or less, twenty or less, forty or less, or other amount of lag less than half. For example, the short lag is less than or up to 20% of the number of transmit apertures (e.g., up to 20% of a length of the array of the transducer where each element is used for a different transmit channel). In one embodiment, the correlation curves for the different locations are summed up to 18% of the array length to produce an SLSC image. For faster scanning, the integration may be up to 11% of the array length. Fewer frames are obtained by using fewer transmit apertures along the array.

In one embodiment, an integral of less than the first twenty, ten, or five lags (e.g., lags 1-5) or other number of lags is calculated. For example, the normalized cross-correlation between each pair of transmit channel frames and an average over all pairs with the same separation are calculated, giving a single value $\rho[z,x,n]$ for each lag value n at every axial and lateral image location. Axial kernels on the order of a wavelength from sample $k_1$ to $k_2$ are used in the cross-correlation and are centered on the sample at depth z. Each pixel $R_{sl}[z, x]$ in the image is created by summing the corresponding coherence curve up to M lags, and normalization is applied to the resulting values. The lag value M is selected as a fraction of the total array length (e.g., M=5) and is a parameter that may be varied to optimize image quality.

Other characteristics of the covariance curve may instead or additionally be calculated, such as slope of the curve. Rather than calculating from a curve, the integral or other value may be calculated directly.

If the data is anisotropic, different coherence values may be obtained depending on whether the integral of the short lag is calculated from different ends of the array or different directions along the array. The short lag spatial coherence may be calculated from both directions and combined. Any combination may be used, such as an average.

After the coherence is calculated for each location or a plurality of locations, an image of the coherence may be generated. The image represents a measure of the covariance or correlation for the locations. Coherence at other locations may be interpolated or extrapolated.

The coherence values may be mapped to grayscale or color values for display. Linear or non-linear mapping is used. Other characteristics of the image may be controlled by the coherence values, such as brightness. The image is of coherence alone. In alternative embodiments, the coherence is an overlay. For example, a B-mode image is generated for a field of view. In a region of interest, the coherence is displayed as gray or color combined with or replacing the B-mode information.

In act 26, the image representing a characteristic of the covariance at the spatial locations is displayed. The gray or color values mapped from the measure are converted, if needed, to the display RGB or other values, and the image is displayed. The image represents the measure of coherence as a function of space. Where the short lag is used, the image is an SLSC image.

FIGS. 6A and 6B show in vivo images of a human liver. FIG. 6A is a synthetic aperture SLSC image using the integration of lags 1-5. The synthetic aperture is the delay correction provided as discussed herein for the FIG. 3A scan format. FIG. 6B shows the image of FIG. 6A, but using only ¼ of the number of transmit elements (apertures). The frame rate may be four times greater. The frames are generated using a delay-and-sum receive beamforming pipeline. Any scan conversion from the scan format to the display format and other image forming post-processing are performed on the image after calculating the coherence.

Figures 7A, 7B, 7C:
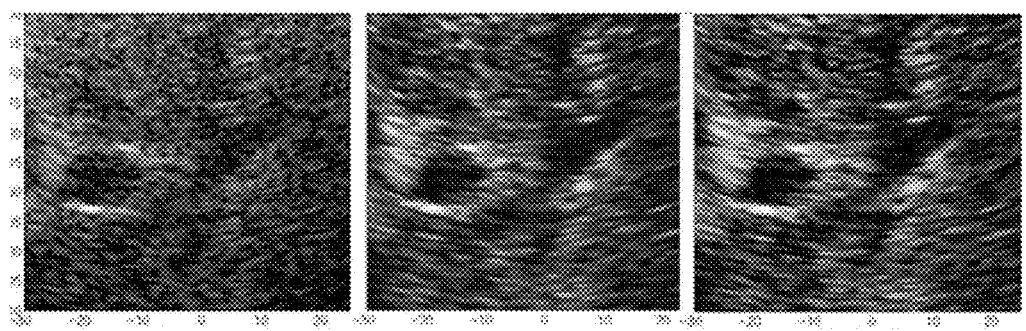
FIG. 7A shows an example enlargement of a synthetic transmit focused B-mode image using beamformed data.
FIGS. 7B and 7C are example enlargements of coherence images.

FIGS. 7B-C show in vivo images cropped to show vessels. FIG. 7A is a B-mode image generated using synthetic transmit aperture processing. The SLSC images of FIGS. 7B-C have less clutter in the vessels than the B-mode image of FIG. 7A.

A commercial clinical scanner may be altered in the post processing portion after beamforming to support coherence-based imaging. Rather than requiring access to channel data, SLSC or other coherence imaging is provided using beamformed frames of data associated with different broad beam transmit apertures. With a real-time, synthetic-aperture channel data stream available, non-linear filtering, compounding, contrast enhancement, or speckle suppression may be used to enhance coherence imaging.

The coherence information may be used for other purposes in addition to or as an alternative to imaging. For example, the beamforming adapts to aberrations. Partially-correlated phase offsets across the array caused by structures in the tissue with varying sound speed may be removed. The coherence information indicates the phase off-sets by spatial location. The individual transmit coherence information may be useful in iterative estimation of the aberration profile. The phase offset is then removed from the recorded data in order to restore the measured coherence that would otherwise be suppressed. In environments such as cardiac imaging where tissue motion may be a concern, the coherence may be used for motion estimation, and the images may be realigned before further processing.

Figure 8:
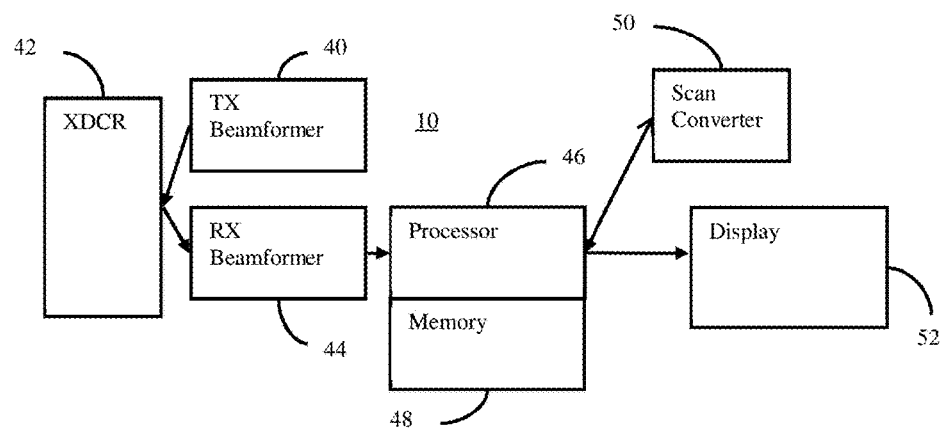
FIG. 8 is a block diagram of one embodiment of a system for coherence ultrasound imaging.

FIG. 8 shows one embodiment of a system 10 for coherence ultrasound imaging. The system 10 is an ultrasound imaging system, but other imaging systems using multiple transmit or receive antennas (i.e., elements) may be used. The system 10 includes a transducer 42, a transmit beamformer 40, a receive beamformer 44, a processor 46, a memory 48, a scan converter 50, and a display 52. In alternative embodiments, the processor 46, memory 48, and/or display 52 are provided as part of a separate computer or workstation. The transducer 42 and beamformers 40 and 44 are part of an ultrasound scanner. The system 10 is configured by hardware and/or software to perform the acts of FIG. 1 or other coherence imaging acts.

Additional, different or fewer components may be provided. For example, the display 52 and/or the scan converter 50 are not provided. Other image processors, filters, or network interfaces may be provided.

The transducer 42 is an array of a plurality of elements. The elements are piezoelectric or capacitive membrane elements. The array is configured as a one-dimensional array, a two-dimensional array, a 1.5D array, a 1.25D array, a 1.75D array, an annular array, a multidimensional array, combinations thereof or any other now known or later developed array. The transducer elements transduce between acoustic and electric energies. The transducer 42 connects with the transmit beamformer 40 and the receive beamformer 44 through a transmit/receive switch, but separate connections may be used in other embodiments.

Two different beamformers are shown in the system 10, the transmit beamformer 40 and the receive beamformer 44. While shown separately, the transmit and receive beamformers 14, 16 may be provided with some or all components in common, such as a controller. Both beamformers connect with the transducer array 12.

The transmit beamformer 40 is a processor, delay, filter, waveform generator, memory, phase rotator, digital-to-analog converter, amplifier, combinations thereof or any other now known or later developed transmit beamformer components. In one embodiment, the transmit beamformer 40 is configured as a single channel or as a plurality of channels for generating electrical signals of transmit waveforms for each element of a transmit aperture on the transducer 42. The waveforms are unipolar, bipolar, stepped, sinusoidal or other waveforms of a desired center frequency or frequency band with one, multiple or fractional number of cycles. The waveforms have relative delay or phasing and amplitude for focusing or defocusing the acoustic energy. The transmit beamformer 40 includes a controller for altering an aperture (e.g. the number and/or position of active elements), an apodization profile across the plurality of channels, a delay profile across the plurality of channels, a phase profile across the plurality of channels, center frequency, frequency band, waveform shape, number of cycles and combinations thereof.

The transmit beamformer 40 is configured to sequentially insonify, using the array. The transmit apertures and corresponding focus and apodization profiles are used to generate broad transmit beams, such as beams with a collimated or parallel beam pattern corresponding to a simulated infinite focus or a beam from one or a few elements. The broad transmit beams insonify a region of the patient from different angles due to being from different transmit apertures.

The receive beamformer 44 is a preamplifier, filter, phase rotator, delay, summer, base band filter, processor, buffers, memory, combinations thereof or other now known or later developed receive beamformer components. The receive beamformer 44 is configured into a plurality of channels for receiving electrical signals representing echoes or acoustic energy impinging on the respective elements of the transducer 42. Beamforming parameters including a receive aperture (e.g., the number of elements and which elements used for receive processing), the apodization profile, a delay profile, a phase profile, frequency, and combinations thereof are applied to the receive signals for receive beamforming. For example, relative delays and amplitudes or apodization focus the acoustic energy along one or more scan lines. A control processor controls the various beamforming parameters for receive beam formation.

In one embodiment, the receive beamformer 44 operates using parallel receive beamformation. The receive signals are provided to multiple beamformer channels for each element. More than one receive beam may be generated in parallel. For example, the receive beamformer 44 forms 16 or more receive beams in response to one broad transmit.

The receive beamformer 44 outputs transmit channel data-data representing different spatial locations of a scanned region in response to a given transmit aperture. The frame of data is coherent (i.e., maintained phase information). The data may be formed by processing received data, such as synthesizing scan lines (i.e., coherent combination), compounding data from multiple scan lines (i.e., incoherent combination) or other processes for generating data used to form an image from received information. For example, inter-beam phase correction is applied to one or more beams and then the phase corrected beams are combined through a coherent (i.e., phase sensitive) filter to form synthesized ultrasound lines and/or interpolated between beams to form new ultrasound lines. Once the channel data is beamformed or otherwise combined to represent spatial locations of the scanned region, the data is converted from the channel domain to the beamformed data domain. The beamformed data may be used for coherence imaging without further access or processing of the channel data.

The scan converter 50 is an application specific integrated circuit, image processor, field programmable gate array, or other device for interpolating data representing one format to another format. In one embodiment, the scan converter 50 is a dedicated scan converter for converting from an acoustic domain to a Cartesian coordinate domain. Frames of beamformed samples in an acoustic domain may be converted to a common grid. Coherent data may be scan converted to the common grid despite being from different transmit apertures. The scan converter 50 outputs scan converted data for display or for further processing by the processor 46. In alternative embodiments, the processor 46 implements the scan converter 50 and/or scan conversion function.

The processor 46 is a general processor, digital signal processor, application-specific integrated circuit, control processor, graphics processing unit, central processing unit, digital circuit, combinations thereof or other now known or later developed processors for controlling the beamformers 40, 44, calculating coherence between frames of data associated with the same region of the patient but different transmit apertures for broad beams, and/or generating a coherence image. The processor 46 includes a single or multiple processors, such as (1) being a graphics processing unit or multiple central processing units or cores for parallel processing to calculate coherence or (2) being a beamformer controller and a separate image processor for coherence calculation. The processor 46 is configured by software or hardware to control scanning, calculate covariance, and/or generating coherence information.

The processor 46 is configured to measure coherence at different locations of the region. The coherence is measured as a covariance or correlation between the beamformed sets of coherent data. In one embodiment, the coherence is measured as a function of a curve of covariance or correlation. The processor 46 calculates the curve as correlation or covariance as a function of lag, and integrates the lag over only a portion of the array, such as integrating for a lag of five and less. Other information may be derived as the coherence between the frames of coherent beamformed data responsive to different broad beam transmits to the same region.

The processor 46 is configured to generate an image of the measure of coherence at the different locations. The values of the coherence measures for different locations are used for imaging a two or three-dimensional region.

The memory 48 is a video random access memory, random access memory, removable media (e.g. diskette or compact disc), hard drive, database, or other memory device for storing frames of beamformed data, calculated covariance, coherence values, and/or images. The memory 48 is used by the processor 46 for coherence imaging.

The instructions for implementing the processes, methods and/or techniques discussed above are provided on non-transitory computer-readable storage media or memories, such as a cache, buffer, RAM, removable media, hard drive or other computer readable storage media, such as represented by the memory 48. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 52 is a CRT, liquid crystal diode, plasma, printer, or other display for outputting an image to a user. The image representing the coherence as a function of space is displayed to the user. For example, a short lag spatial coherence image is provided on the display 52. The short lag spatial coherence information is provided by calculating coherence across beamformed frames of data rather than receive element channels. Transmit channel frames are used instead.

Acoustic reciprocity allows use of transmit channel information instead of receive channel information for coherence imaging. The roles of the transmit and receive apertures are exchanged to derive the coherence as a function of transmit channel separation or lag. Assumptions of a sub-wavelength incoherent scattering medium and separability are made. The desired function is the spatial covariance of the pressure field transmitted from two points $X_1$ and $X_2$ at the frequency f, scattered by the medium and received on the same array.

The measured pressure P is described by a linear system of three parts—forward propagation, scattering, and backwards propagation. A pressure wave with frequency f is transmitted from a single element at location $X_1$, interacts with a scatterer at location $X_0$, and returns an echo to the transducer. A constant representing the transmit pressure amplitude is omitted from this expression.

$$P(X_0, X_1, f) = H_{tx}(X_0, X_1, f)\chi(X_0, f)H_{rx}(X_0, f) \quad (1)$$

where $H_{tx}$ is the transmit spherical wave and $H_{rx}$ is the receive spherical wave.

The phase of the signal arriving at the scattering media point $X_0$ from the array point $X_1$ is an incident pressure due to a single point source. The incident pressure due to a single point source on the aperture with unity weighting is described by the spherical wave $H_{tx}(X_0, X_1, f)$.

$$H_{tx}(X0, X1, f) = \frac{e^{j2\pi f r_{01}/c}}{r_{01}} \quad (2)$$

$$r_{01} = |X_0 - X_1|$$

where r is distance between the transmit element and the receive element.

The pressure field emitted by a single scatter described by the scattering function $\chi(X_0, f)$ is a spherical wave. The pressure is received at an array located a distance r away and summed over the entire array with aperture weighting function O(X), giving:

$$H_{rx}(X0, X1, f) = \int\int_O O(X)\frac{e^{j2\pi f r_{01}/c}}{r_{01}} d^2X \quad (3)$$

$$r = |X - X_0|$$

Integrating the scattered pressure field from the entire medium gives the total received pressure signal.

$$P(X_1, f) = \iiint_V P(X_0, X_1, f)d^3X_0 \quad (4)$$

The spatial covariance $R_p(X_1, X_2, f)$ is the expected value of the inner product between the pressure from two source points.

$$R_p(X_1, X_2, f) = \langle P(X_1, f)P^*(X_2, f)\rangle \quad (5)$$

$$P(X_1, f)P^*(X_2, f) = \quad (6)$$
$$\iiint_V \iiint_V \chi(X_1', f)\chi^*(X_2', f)xH_{rx}(X_1', f)$$
$$H_{rx}^*(X_2', f)\frac{e^{\frac{j2\pi f r_1' - r_2'}{c}}}{r_1' r_2'} d^3X_1' d^3X_2'$$

$$r_i' = |X_i - X_i'|$$

The spatially-incoherent scattering terms are used to simplify the integral, reducing the expression to a single volume integral. The covariance is expressed as the frequency-dependent scattering function, the magnitude of the receive transfer function, and a phase term.

$$R_p(X_1, X_2, f) = X_0(f)\iiint_V |H_{rx}(X, f)|^2 x \frac{e^{\frac{j2\pi f r_1' - r_2'}{c}}}{r_1' r_2'} d^3X \quad (7)$$

$$r_i' = |X_i - X_i'|$$

The Fresnel approximation is made assuming that the depth between two points $X_1 = (x_1, 0)$ and $X = (x, z)$ is large compared to the lateral distances.

$$r \approx z + (1/2z)(x_1 - x) \cdot (z_1 - z) \quad (8)$$

Using this approximation in the phase term, simplifying to r≈2 in the amplitude terms, and taking the depth z to be constant, the final expression shows the familiar form of the van Cittert-Zernike theorem.

$$R_p(X_1, X_2, z, f) = \quad (9)$$
$$\frac{\chi_0(f)}{z^2}e^{j\pi f[x_1 \cdot z_1 - x_2 \cdot z_2)/zc]}x\iint_S |H_{rx}(x, z, f)|^2 e^{-j2\pi f[x \cdot (x_1 - x_2)]/zc} d^2x$$

When the two points are symmetrical to the center of the transducer ($x_1 = -x_2$), this reduces to the two-dimensional Fourier transform of the receive transfer function term taken with respect to the frequency $(x_1 - x_2)/\lambda_z$. The expected coherence of ultrasound in tissue demonstrates reciprocity of the transmit and receive apertures. Given a unity aperture function for both transmit and receive apertures, the expected coherence between either receive channels or transmit channels is a ramp function.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for coherence ultrasound imaging, the method comprising:
    transmitting, from a transducer, first and second broad transmit beams at different angles, the first and second broad transmit beams covering an overlapping region;
    receiving first and second sets of signals responsive to the first and second transmit beams, respectively, with the transducer, the sets of signals comprising channel data from different elements of the transducer;
    beamforming, with a beamformer, first and second frames of beamformed data representing the overlapping region from the first and second sets of signals, respectively, the beamforming combining the channel data through summation into the beamformed data;
    calculating, with a processor, covariance or correlation between the beamformed data of the first and second frames for each of a plurality of locations in the overlapping region; and
    generating an image of a characteristic of coherence based on the covariance or correlation for each of the locations.

2. The method of claim 1 wherein transmitting comprises transmitting from first and second single elements of the transducer.

3. The method of claim 1 wherein transmitting comprises transmitting at least 64 broad transmit beams, including the first and second, from different transmit apertures spaced along an array of the transducer, and wherein receiving comprises receiving at least 64 sets of signals, including the first and second sets, with a same receive aperture.

4. The method of claim 1 wherein the channel data comprises channel signals from the elements of the transducer, and wherein beamforming comprises summing the channel signals from every element of a receive aperture together for each of the plurality of locations with dynamic focusing.

5. The method of claim 1 wherein beamforming comprises beamforming along a rectilinear field of view; and further comprising retrospectively transmit focusing the data of the first and second frames.

6. The method of claim 1 wherein beamforming comprises beamforming over a fan format; and
    further comprising scan converting the first and second frames of data to a common grid of the locations.

7. The method of claim 1 wherein calculating comprises calculating a normalized cross-correlation.

8. The method of claim 1 wherein calculating comprises calculating the covariance.

9. The method of claim 1 wherein the first and second frames of data comprise coherent data, and wherein calculating comprises calculating correlation or covariance curves as a function of transmit beams including the first and second transmit beams.

10. The method of claim 1 wherein generating the image of the characteristic comprises generating the image with a lag of 20 or less of the covariance or correlation as the characteristic.

11. The method of claim 10 wherein generating the image with the lag of 20 or less comprises generating with the lag of 5 or less from both directions along an array of the transducer.

12. The method of claim 1 wherein generating the image of the characteristic comprises generating the image with the characteristic comprising an integral of a curve for up to 20% of a length of an array of the transducer.

13. The method of claim 1 wherein generating the image comprises generating the image with gray or color values mapped from the characteristic.

14. The method of claim 1 wherein calculating comprises calculating the covariance or correlation across frames of beamformed data, including the first and second frames, from different transmit apertures.

15. The method of claim 1 wherein calculating comprises calculating the covariance or correlation using spatial kernels centered on the locations.

16. The method of claim 1 wherein generating the image comprises generating an incoherent isotropic object image.

17. The method of claim 1 wherein generating the image comprises generating a specular anisotropic object image.

18. The method of claim 1 wherein generating the image comprise generating a direction of anisotropic object image.

19. The method of claim 1 wherein beamforming comprises forming the first and second frames of beamformed data as first and second transmit channel frames of focused data corresponding to the first and second broad transmit beams.

* * * * *